United States Patent [19]

Frazer et al.

[11] 4,130,579

[45] Dec. 19, 1978

[54] BIS(2-METHYL-2-CYANOPROPYL) AROMATICS

[75] Inventors: August H. Frazer; John F. Harris, Jr.; Elmore L. Martin, all of Wilmington, Del.

[73] Assignee: E. I. Du Pont de Nemours and Company, Wilmington, Del.

[21] Appl. No.: 804,855

[22] Filed: Jun. 8, 1977

[51] Int. Cl.² .......................................... C07C 121/66
[52] U.S. Cl. ........................ 260/465 H; 260/465 F; 260/465 G; 260/570 R; 260/570.8 R; 528/347; 528/349; 528/348; 528/299; 528/298; 528/307; 528/183

[58] Field of Search ............ 260/465 H, 465 G, 465 F

[56] References Cited

U.S. PATENT DOCUMENTS

| 2,497,673 | 2/1950 | Kirk, Jr. ...................... 260/465 H X |
| 2,891,088 | 6/1959 | Condo et al. ................... 260/465 H |
| 3,755,412 | 8/1973 | Taranko et al. ................. 260/465 H |

FOREIGN PATENT DOCUMENTS 938787 10/1973 United Kingdom.

OTHER PUBLICATIONS

Stephens, Journal of Polymer Science, vol. XL, pp. 359-366 (1959).

*Primary Examiner*—Dolph H. Torrence

[57] ABSTRACT

Aromatic-aliphatic dinitriles of the formula

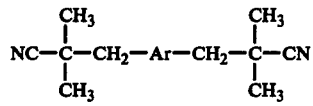

in which Ar is an arylene or substituted arylene are useful in the preparation of the corresponding amines which are intermediates for the preparation of thermally stable, rigid, polyamides.

6 Claims, No Drawings

BIS(2-METHYL-2-CYANOPROPYL) AROMATICS

BACKGROUND OF THE INVENTION

1. Field of the Invention

This invention relates to aliphatic dinitriles, and more particularly to aromatic-aliphatic dinitriles containing no hydrogen atoms alpha to the cyano groups.

2. Description of the Prior Art

Neopentyl diamine is known and polyamides have been made from this diamine.

SUMMARY OF THE INVENTION

There have now been discovered aromatic-aliphatic dinitriles of the formula

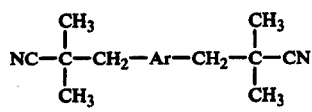

where Ar is an arylene selected from the group consisting of 1,2-phenylenes, 1,3-phenylenes, 1,4-phenylenes, 2,2'-biphenylenes, 3,3'-biphenylenes, 4,4'-biphenylenes, 4,4'-phenyleneoxyphenylenes, 4,4'-phenylenemethylenephenylenes and 2,6-naphthylenes, said arylene being unsubstituted or substituted with halo, lower alkyl or phenyl. These dinitriles are useful for the preparation of the corresponding diamines which are intermediates for the preparation of thermally stable, rigid polyamides.

The term "halo" is intended to include chloro, bromo, fluoro and iodo. The term "lower alkyl" is intended to include alkyls of 1 to 6 carbon atoms. The substituted phenylene may have 1 to 4 of the specified substituents, the substituted biphenylene and phenyleneoxyphenylene may have 1 to 8 of these substituents, the substituted phenylenemethylenephenylene may have 1 to 10 of these substituents, and the substituted naphthylene may have 1 to 6 of these substituents. The term "rigid" is used in conjunction with polymers to denote the presence of a sufficient quantity of aromatic rings in the backbone of the polymer to provide stiffness.

DESCRIPTION OF THE PREFERRED EMBODIMENTS

The dinitriles of this invention are prepared by reacting the lithium salt of isobutyronitrile, generated in situ, with an α,α'-dihaloaromatic compound of the formula

in which Ar is arylene as defined above, and X is Br or Cl at a temperature low enough to prevent the undesired decomposition of the lithium salt, e.g., in the range of −50° to −100° C., in a medium which at the appropriate temperature is a satisfactory solvent for both the lithium salt and the α,α'-dihaloaromatic compound, and under an inert dry atmosphere, e.g., nitrogen, helium, argon and the like, according to the following equation:

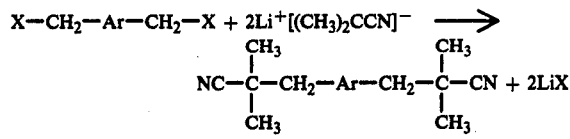

The solvent must also be nonreactive with the lithium salt, and its progenitors, e.g., it must be nonprotic. Ethers, especially cyclic ethers, e.g., tetrahydrofuran, are preferred solvents.

The lithium salt is generated in the reaction medium at the appropriate temperature by first reacting a hindered secondary amine, such as diisopropylamine, with a lower alkyllithium, such as n-butyllithium, to bring about the formation of the lithium salt of the hindered secondary amine, followed by addition of anhydrous isobutyronitrile. After allowing an appropriate time for the reaction to take place at the prescribed temperature, e.g., at least several hours, the reaction mixture is allowed to warm to room temperature, and the product is isolated and purified by conventional methods.

The arylene groups embraced in the definition of Ar above are readily obtained by selection of the α,α'-dihaloaromatic compound. For example, suitable compounds include:

α,α'-dibromo-m-xylene
α,α'-dibromo-p-xylene
α,α'-dibromo-o-xylene
α,α'-dichloro-m-xylene
α,α'-dibromo-2-chloro-p-xylene
α,α'-dibromo-2-methyl-p-xylene
α,α,-2-tribromo-p-xylene
3,6-bis(chloromethyl)durene
2,2'-bis(bromomethyl)biphenyl
2,2'-bis(chloromethyl)biphenyl
4,4'-bis(bromomethyl)-3,3'-difluorobiphenyl
3,3'-dichloro-4,4'-bis(bromomethyl)biphenyl
3-chloro-4,4'-bis(bromomethyl)biphenyl
2,6-bis(bromomethyl)naphthalene
2,6-bis(chloromethyl)naphthalene
1,5-dichloro-2,6-bis(bromomethyl)naphthalene
1-chloro-2,6-bis(bromomethyl)naphthalene
3,3'-bis(bromomethyl)biphenyl
4,4'-bis(bromomethyl)biphenyl
4,4'-bis(chloromethyl)biphenyl
4,4'-bis(bromomethyl)diphenyl oxide
4,4'-bis(chloromethyl)diphenyl oxide
4,4'-bis(bromomethyl)diphenylmethane
4,4'-bis(chloromethyl)diphenylmethane
and the like.

The diamines corresponding to the dinitriles of this invention are prepared by heating the dinitrile with a dialkylaluminum hydride, preferably diisobutylaluminum hydride, for several hours in an inert anhydrous nonprotic solvent, e.g., a hydrocarbon and preferably an aromatic hydrocarbon, at a temperature sufficiently elevated above room temperature so that the reaction occurs at a convenient rate, e.g., 120° C., under a dry inert atmosphere, e.g., nitrogen, argon, helium and the like. After the reaction period is over, the intermediate aluminum salts are hydrolyzed by the gradual addition of a solution of water in a lower aliphatic alcohol, e.g., methanol. The following equations presumably represent the steps involved.

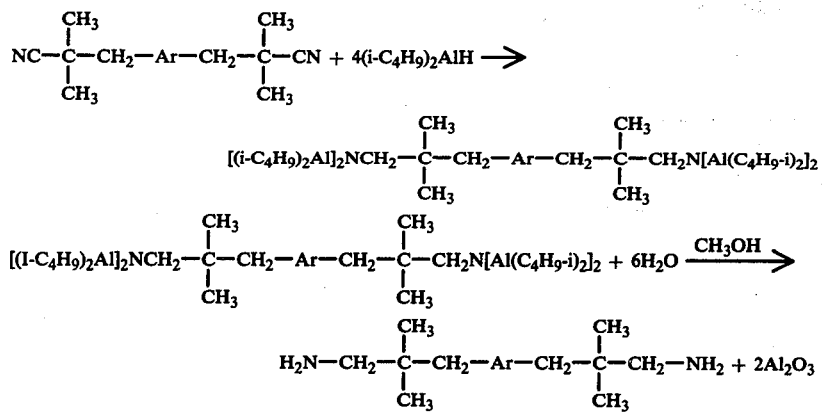

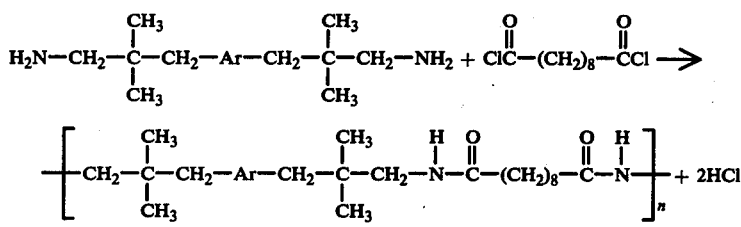

The by-product hydrated aluminum oxide is removed by filtration and the desired diamine is isolated and purified by conventional means.

The polyamides are prepared by reacting the diamines with either acid chlorides of dibasic acids in the presence of an acid acceptor, or with diphenyl esters of dibasic acids. With the acid chlorides of aliphatic dibasic acids, e.g., sebacyl chloride, $$H_2N-CH_2-\underset{\underset{CH_3}{|}}{\overset{\overset{CH_3}{|}}{C}}-CH_2-Ar-CH_2-\underset{\underset{CH_3}{|}}{\overset{\overset{CH_3}{|}}{C}}-CH_2-NH_2 + Cl\overset{O}{\overset{\|}{C}}-(CH_2)_8-\overset{O}{\overset{\|}{C}}Cl \longrightarrow$$

$$\left[ -CH_2-\underset{\underset{CH_3}{|}}{\overset{\overset{CH_3}{|}}{C}}-CH_2-Ar-CH_2-\underset{\underset{CH_3}{|}}{\overset{\overset{CH_3}{|}}{C}}-CH_2-\overset{H}{\overset{|}{N}}-\overset{O}{\overset{\|}{C}}-(CH_2)_8-\overset{O}{\overset{\|}{C}}-\overset{H}{\overset{|}{N}} \right]_n + 2HCl$$

a convenient method for preparing the polyamides comprises a solution polymerization in which a solution of the acid chloride in an inert nonprotic solvent, e.g., chloroform, carbon tetrachloride, and the like, is added quickly to a stirred solution of the diamine and a tertiary amine, e.g., triethylamine, as the acid acceptor, in the same solvent. These condensation polymerizations are usually carried out at ambient temperature, but higher or lower temperatures are also satisfactory. The isolation of the product usually involves the addition of a nonsolvent for the polymer, followed by thorough washing of the polymer in water. These procedures are discussed by P. W. Morgan in "Condensation Polymers by Interfacial and Solution Methods" Wiley, 1965.

A convenient method for the preparation of polyamides from the acid chlorides of aromatic dibasic acids, e.g., terephthaloyl chloride, involves an interfacial polymerization technique in which the diamine is dispersed in a rapidly stirred mixture of water, an inert water-immiscible solvent, e.g., chloroform, carbon tetrachloride and the like, a dispersing agent, e.g., sodium lauryl sulfate, and a water soluble acid acceptor, e.g., sodium carbonate. The acid chloride, dissolved in the same inert, water-immiscible solvent, is then added rapidly. Such procedures and the methods for isolating and purifying the products are also described by P. W. Morgan in the reference noted above.

Suitable acid chlorides of dibasic acids for reacting with the diamines to prepare the polyamides include:
adipyl dichloride
sebacyl dichloride
malonyl dichloride
isophthaloyl dichloride
terephthaloyl dichloride
chloroterephthaloyl dichloride
methylterephthaloyl dichloride
ethylterephthaloyl dichloride
5-tert-butylisophthaloyl dichloride
tetrafluoroterephthaloyl dichloride
tetrachloroterephthaloyl dichloride
tetrabromoterephthaloyl dichloride
tetraiodoterephthaloyl dichloride
tetramethylterephthaloyl dichloride
2,5-diphenylterephthaloyl dichloride
4,4'-biphenyldicarbonyl dichloride
2,2',3,3',5,5',6,6'-octafluoro-4,4'-biphenyldicarbonyl dichloride
2,2'-dibromo-4,4'-biphenyldicarbonyl dichloride
2,2',6,6'-tetrachloro-4,4'-biphenyldicarbonyl dichloride
2,2'-diiodo-4,4'-biphenyldicarbonyl dichloride
2,2'-dimethyl-4,4'-biphenyldicarbonyl dichloride
4,4'-oxydibenzoyl dichloride
3,3'-dimethyl-4,4'-oxydibenzoyl dichloride
2,6-naphthalenedicarbonyl dichloride
1,3,4,5,7,8-hexachloro-2,6-naphthalenedicarbonyl dichloride
1,4-cyclohexanedicarbonyl dichloride
1-methyl-2,3-cyclobutanedicarbonyl dichloride
bis(4-chlorocarbonylphenyl)methane
bis(4-chlorocarbonylphenyl)dichloromethane
2,2'-bis(4-chlorocarbonylphenyl)propane
and the like.

To prepare polyamides by reactions of the diamines with diphenyl esters, it is only necessary to intimately mix the diamine and the diphenyl ester in a suitable vessel and then apply heat so that an exchange reaction occurs with the expulsion of phenol:

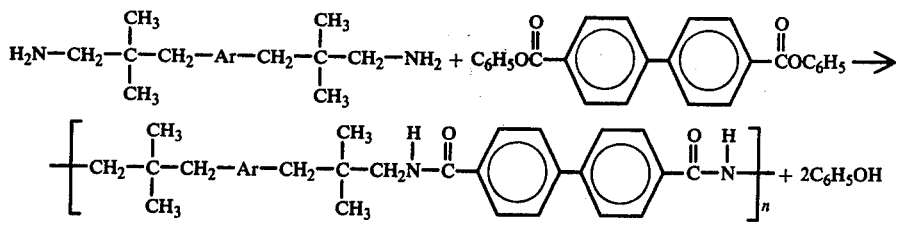

At temperatures of about 200° C. and higher the reaction occurs at a convenient rate, and is completed in a few hours. The temperature can be raised in the later portion of the reaction period to facilitate the driving off of by-product phenol. The removal of phenol is also facilitated by evacuation of the reaction vessel, e.g., with an oil pump. When the reaction is completed, the polymer is isolated and purified by conventional methods. Exchange reactions for the preparation of polyamides from diamines and the aryl esters of dibasic acids are described in "Encyclopedia of Polymer Science and Technology", Vol. 10, pg. 487, Wiley, 1969. The diphenyl esters corresponding to the diacid chlorides listed above may be used in this exchange reaction with the diamines to prepare the polyamides.

Because the dinitriles of this invention are free of hydrogen atoms alpha to the cyano groups, the polyamides, prepared from the corresponding diamines are much superior in thermal stability to the corresponding polyamides having hydrogen atoms beta to nitrogen. This is particularly advantageous in melt processing these polyamides, for example, in melt spinning of fibers. The most thermally stable of these polyamides, and therefore a preferred group, are the polyamides derived from aromatic diacids.

EXAMPLES OF THE INVENTION

The following examples illustrate the novel dinitriles of this invention and their utility for preparing useful polyamides. In these examples parts are by weight unless otherwise indicated, and all temperatures are expressed in degrees Centigrade. All equipment was dried in an oven at 135° before assembly and flushed with dry nitrogen after assembly. Weighing and handling of all the diamines was carried out in a nitrogen dry box. The alcohol used in these examples was 95% ethanol denatured with benzene.

EXAMPLE 1

1,4-Bis(2-methyl-2-cyanopropyl)benzene

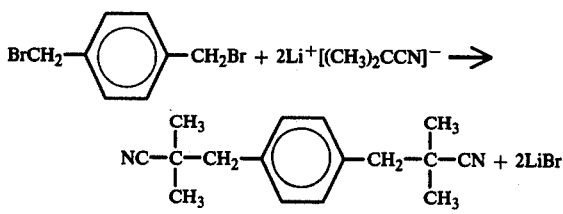

In a 2-liter flask, equipped with a magnetic stirrer, a reflux condenser capped with a nitrogen bubbler, a dropping funnel, and a syringe adapter, was placed 900 ml of anhydrous tetrahydrofuran (THF) and 42 ml (30.32 g, 0.30 M) of diisopropylamine (via syringe). The stirred mixture was cooled in a dry ice-acetone bath, and then 138.6 ml of 2.17 N (0.30 M) n-butyllithium in hexane was added via syringe. After the mixture had stirred for 1 hr, a solution of 20.52 g (0.297 M) of freshly distilled isobutyronitrile in 60 ml of anhydrous THF was added in 20 minutes. Following an additional 1 hr and 7 min. of stirring at dry ice temperature, a solution of 39.57 g (0.150 M) of α,α'-dibromo-p-xylene in 450 ml of anhydrous THF was added in 1 hr 23 min. The mixture was stirred at dry ice temperature for 2 hr 15 min. and then overnight as the cooling bath warmed to room temperature. Stirring was continued for 4 days at room temperature. The suspended white solid was removed by filtration, rinsed on the filter with THF and dried: wt = 13.74 g, mp = 193°–195°. The filtrate was distilled on the water pump to remove the solvent, and the residue, a mixture of brown oil and solid, was stirred with 100 ml of methanol which dissolved the brown oil. Filtration of the mixture, rinsing of the solid on the filter with methanol, and drying of the solid under nitrogen gave an additional 15.7 g of crude 1,4-bis(2-methyl-2-cyanopropyl)benzene melting at 192°–194.5° (total yield = 82%). Dissolving of this material in refluxing acetone (28.5 ml/g), filtration of the hot solution through a coarse sintered glass funnel to remove some insoluble material, and cooling of the filtrate at 8°–10° gave the product as colorless needles melting at 194°–195°.

Anal. Calcd. for $C_{16}H_{20}N_2$: C, 79.95; H, 8.39; N, 11.66. Found: C, 79.79; 79.96 H, 8.21; 8.37 N, 11.83 11.67.

EXAMPLE 2

1,3-Bis(2-methyl-2-cyanopropyl)benzene

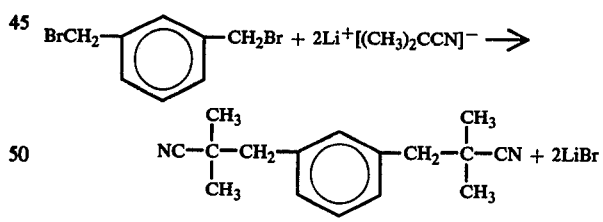

In a dry 2-liter flask, equipped with a large magnetic stirrer, a reflux condenser capped with a nitrogen bubbler, an addition funnel, and a syringe adapter, was placed 900 ml of anhydrous THF and 42 ml (30.32 g, 0.300 M) of diisopropylamine (via syringe). The mixture was cooled in a dry ice-acetone bath and, with stirring, 125.3 ml of 2.4 molar (0.300 M) n-butyllithium in hexane was added via syringe. After the mixture had stirred for 1 hr 35 min, 20.52 g (0.297 M) of freshly distilled isobutyronitrile in 60 ml of THF was added in 30 minutes. Following another 70 minutes of stirring, 39.57 g (0.150 M) of α,α'-dibromo-m-xylene was added all at once. The mixture was stirred for 2 hrs at −76°, and then overnight as the cooling bath warmed to room temperature. After an additional day of stirring at room temperature, the mixture was distilled on the water pump to yield a semisolid residue. Dissolving this material in 700 ml of chloroform, followed by three extractions of the resulting solution with 200 ml of water (with HCl acidification during the first extraction), drying over anhydrous magnesium sulfate, and removal of the solvent on the water pump, gave 35.5 g (98%) of a slowly crystallizing, brown solid. This material was further dried on an oil pump: mp = 58°–63°. All of this material was stirred with 2 liters of refluxing cyclohexane, but an appreciable quantity of an oily material was insoluble. Decanting of the solution from this oil, followed by cooling, yielded 18.0 g of 1,3-bis(2-methyl-2-cyanopropyl)benzene as almost colorless prisms melting at 69°–70°. Refluxing of the filtrate with Darco, followed by filtration, evaporation to about 500 ml, seeding, and cooling, yielded an additional 9.16 g of product melting at 68°–70°.

Anal. Calc'd for $C_{16}H_{20}N_2$: C, 79.95; H, 8.39; N, 11.66 Found: C, 79.88; 79.69 H, 8.04; 8.31 N, 11.74 11.56.

EXAMPLE 3

1,4-Bis(2-methyl-2-cyanopropyl)tetramethylbenzene

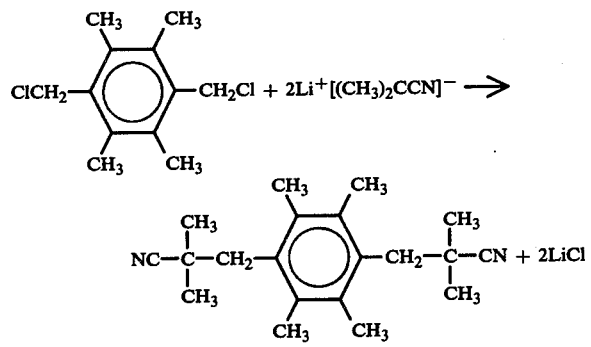

In a 1-liter flask, equipped with a magnetic stirrer, a reflux condenser capped with a nitrogen bubbler, an addition funnel, and a syringe adapter, was put 500 ml of anhydrous THF and 14 ml (10.10 g, 0.10 M) of diisopropylamine (via syringe). The flask was cooled in a dry ice-acetone bath and, with stirring, 41.8 ml of 2.4 molar (0.100 M) n-butyllithium in hexane was added via a syringe. The mixture was stirred for 1 hr, and then a solution of 6.48 g (0.094 M) of freshly distilled isobutyronitrile in 20 ml of anhydrous THF was added in 20 minutes. After an additional 65 minutes of stirring, 11.55 g (0.050 M) of 3,6-bis(chloromethyl)durene was added all at once. The mixture was stirred for 5 hrs at −76°, and then overnight as the cooling bath warmed to room temperature. Filtration of the solid, rinsing on the filter with THF, and drying under nitrogen, yielded 8.50 g of crude 1,4-bis(2-methyl-2-cyanopropyl)tetramethylbenzene melting at 187°–190°. Evaporation of the filtrate to dryness yielded additional solid which was dissolved in 325 ml of chloroform. Extraction of this solution three times with 100 ml of water (with HCl-acidification during the first extraction), drying of the chloroform solution over anhydrous magnesium sulfate, and removal of the solvent in vacuo, yielded an additional 5.30 g of crude product (93% total yield) melting at 162°–180°. Recrystallization of this material from acetone yielded the product as colorless needles melting at 192.5°–193°.

Anal. Calc'd for $C_{20}H_{28}N_2$: C, 81.03; H, 9.52; N, 9.45. Found: C, 81.31; 81.14 H, 9.35; 9.57 N, 9.46 9.41.

The infrared spectrum of this material contains bands at 3.31μ (=CH), 3.35 and 3.40μ (saturated CH), 4.48μ (—C≡N), 6.69μ (aromatic C=C) and 7.18 and 7.30μ (gem-dimethyl).

EXAMPLE 4

3,3′-Bis(2-methyl-2-cyanopropyl)biphenyl

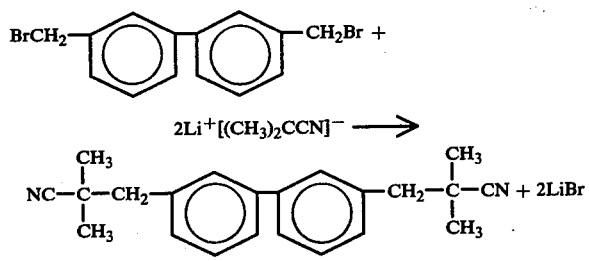

In a 500-ml flask, equipped with a magnetic stirrer, a reflux condenser capped with a nitrogen bubbler, a dropping funnel and a syringe adapter, was put 150 ml of anhydrous THF and 7.0 ml (5.05 g, 0.050 M) of diisopropylamine (via syringe). The flask was cooled in a dry ice bath, and with stirring, 23.1 ml of 2.17 molar (0.050 M) n-butyllithium in hexane was added via syringe. The mixture was stirred for 55 minutes, and then a solution of 3.42 g (0.049 M) of freshly distilled isobutyronitrile in 10 ml of anhydrous THF was added dropwise in 7 minutes. After an additional 20 minutes of stirring, a solution of 8.50 g (0.0250 M) of 3,3′-bis(bromomethyl)biphenyl in 75 ml of anhydrous THF was added during 38 minutes. The mixture was allowed to warm to room temperature as it stirred overnight. During the addition, the mixture developed an intense blue color. This color was still apparent on the day after the mixture had warmed to room temperature, but after two additional days of stirring at room temperature, the mixture was light brown and clear. The solvent was removed on the water pump and the resulting residue was dissolved in 200 ml of chloroform. Washing of this solution three times with 100 ml of water (with HCl acidification during the first washing), drying the solution over anhydrous magnesium sulfate, removal of the solvent on the water pump, and drying the resulting residue in vacuo, gave 7.50 g (95%) of crude 3,3′-bis(2-methyl-2-cyanopropyl)biphenyl melting at 96°–103°. Dissolving this material in hot cyclohexane, refluxing the resulting solution with Darco, filtering through Celite, evaporating the filtrate to 125 ml, and cooling it at 8°–10°, gave 5.36 g of the product as colorless prisms melting at 106.5°–108.5°.

Anal. Calc'd for $C_{22}H_{24}N_2$: C, 83.50; H, 7.64; N, 8.86 Found: C, 83.74; 83.57 H, 7.60; 7.53 N, 8.63 8.60.

The infrared spectrum (KBr) contains bands at 3.25μ (=CH), 3.32, 3.37 and 3.44μ (saturated CH), 4.45μ (—C≡N), 6.19 and 6.28 μ (aromatic C=C) and 12.7 and 14.04μ (meta disubstituted benzene).

EXAMPLE 5

2,6-Bis(2-methyl-2-cyanopropyl)naphthalene

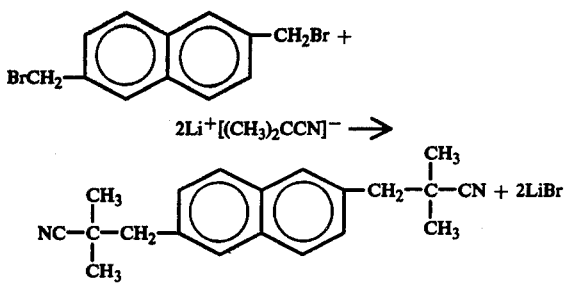

In a 1-liter flask, equipped as described in Example 4, was put 400 ml of anhydrous THF and 14.00 ml (10.10 g, 0.10 M) of diisopropylamine. The flask was cooled in a dry ice bath and, with stirring, 48.3 ml of 2.29 molar (0.111 M) n-butyllithium in hexane was added via a syringe. The mixture was stirred for 75 minutes and then 6.84 g of freshly distilled isobutyronitrile in 20 ml of anhydrous THF was added during 12 minutes. After an additional 23 minutes of stirring, 15.2 g of 2,6-bis(-bromomethyl)naphthalene was added all at once. The mixture was stirred at −76° for 2¼ hrs and then overnight as the bath warmed to room temperature. After an additional 3¼ days of stirring at room temperature, the mixture was filtered and the resulting solid was rinsed on the funnel with THF and dried under nitrogen: wt = 3.13 g, mp = 181.8°–184°. Evaporation of the filtrate to dryness on the water pump yielded additional solid which was dissolved in 700 ml of chloroform. Extraction of the chloroform solution three times with 300 ml of water (with HCl acidification during the first extraction), and removal of the solvent in vacuo yielded additional crude product, which after drying in a vacuum oven at room temperature, weighed 10.00 g and melted at 178°–180°. Recrystallization of this material from acetone yielded 2,6-bis(2-methyl-2-cyanopropyl)naphthalene melting at 183.5°–184.5°.

Anal. Calc'd for $C_{20}H_{22}N_2$: C, 82.71; H, 7.64; N, 9.65 Found: C, 83.21; 82.93 H, 7.84; 7.73 N, 9.70 9.62.
The infrared spectrum of this material contains a C≡N stretch band at 4.45μ.

EXAMPLE 6

Preparation of 4,4'-Bis(2-methyl-2-cyanopropyl)biphenyl

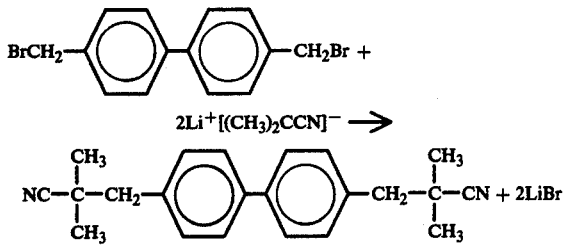

In a 500-ml flask, equipped as described in Example 4, was placed 250 ml of anhydrous THF and 7.00 ml of diisopropylamine (via syringe). The flask was cooled in a dry ice bath and, with stirring, 21.0 ml of 2.4 molar n-butyllithium in hexane was added via a syringe. The mixture was stirred for 1 hour and then 3.42 g of freshly distilled isobutyronitrile in 20 ml of THF was added in 20 minutes. After an additional hour of stirring, 8.50 g of 4,4'-bis(bromomethyl)biphenyl was added all at once. Stirring at −76° was continued for several hours and overnight as the cooling bath warmed to room temperature. After an additional day of stirring, the solvent was distilled on the water pump. The resulting semisolid residue was dissolved in 500 ml of chloroform and the chloroform solution was extracted 4 times with water (with HCl acidification during the first extraction). Drying the solution over anhydrous magnesium sulfate, filtering, and removal of the solvent in vacuo gave 6.8 g of crude 4,4'-bis(2-methyl-2-cyanopropyl)biphenyl melting at 174°–182°. After several recrystallizations from acetone, the product melted at 189.3°–190.8°.

Anal. Calc'd for $C_{22}H_{24}N_2$: C, 83.50; H, 7.64; N, 8.86 Found: C, 82.81; 83.43 82.94 H, 7.94; 7.86 7.90 N, 8.69 8.79 8.80.

EXAMPLE 7

3,3'-Dichloro-4,4'-bis(2-methyl-2-cyanopropyl)biphenyl

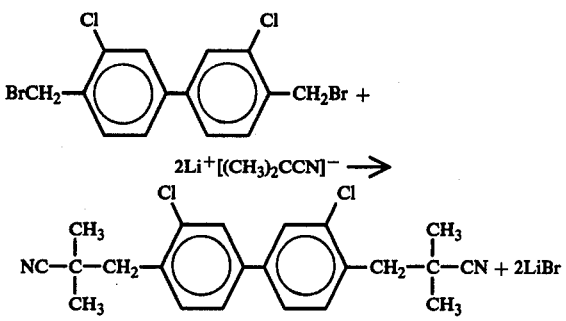

In a 500-ml flask, equipped as described in Example 4, was placed 150 ml of anhydrous THF and 7.0 ml of diisopropylamine (via syringe). The flask was cooled at −76° and, with stirring, 21.0 ml of 2.4 molar n-butyllithium in hexane was added via syringe. The mixture was stirred for 1 hr 25 min and the 3.42 g of freshly distilled isobutyronitrile in 10 ml of THF was added in 20 minutes. After an additional 25 minutes of stirring, a solution of 10.22 g of 3,3'-dichloro-4,4'-bis(bromomethyl)biphenyl in 100 ml of THF was added with stirring during 1 hr 20 min. The mixture was stirred at −76° for 1 hr 45 min and then overnight as the cooling bath warmed to room temperature. After an additional 2 days of stirring at room temperature, the solvent was removed in vacuo. The resulting residue was dissolved in 200 ml of chloroform and the chloroform solution was extracted 3 times with 100 ml of water (with HCl acidification during the first extraction). Drying the solution over anhydrous magnesium sulfate, filtering, and removal of the solvent in vacuo, gave 7.5 g of crude 3,3'-dichloro-4,4'-bis(2-methyl-2-cyanopropyl)biphenyl melting at 148°–156°. A recrystallization from acetone, with a filtration of the hot solution to remove some insoluble material, gave product melting at 162°–164°.

Anal. Calc'd for $C_{22}H_{22}Cl_2N_2$: C, 68.57; H, 5.76; Cl, 18.40; N, 7.27. Found: C, 68.36; 68.80 68.28 H, 5.93; 6.09 5.69 Cl, 18.14; 18.34 N, 7.48 7.19.

EXAMPLE 8

1-Bis(2-methyl-2-cyanopropyl)benzene

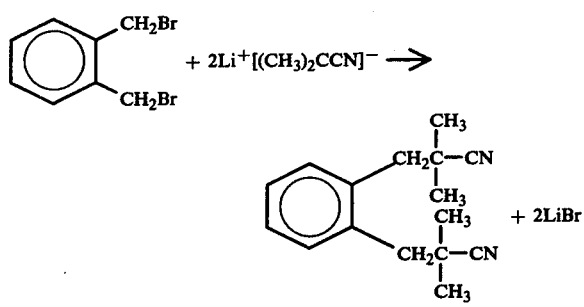

In a dry 1-liter flask, equipped with a large magnetic stirrer, a reflux condenser capped with a nitrogen bubbler, an addition funnel, and a syringe adapter, was placed 570 ml of anhydrous THF, and 26.5 ml of diisopropylamine (via syringe). The mixture was cooled in a dry ice bath, and with stirring, 73.1 ml of 2.6 molar n-butyllithium in hexane was added via syringe. After the mixture had stirred for 1 hr, a solution of 13.1 g of freshly distilled isobutyronitrile in 40 ml of THF was added in 25 min. Following another 35 min of stirring, 25.0 g of α,α'-dibromo-o-xylene was added all at once. The mixture was stirred for 1 hr at −76°, and then overnight as the dry ice bath warmed to room temperature. After an additional 2 days of stirring at room temperature, the mixture was distilled on the water pump to remove the solvent. Dissolving of the resulting residue in 400 ml of chloroform, followed by 3 extractions of the chloroform solution with 200 ml of water (with HCl acidification during the first extraction), drying over anhydrous magnesium sulfate, and removal of the solvent on the water pump, gave 21.50 g (94%) of crude 1,2-bis(2-methyl-2-cyanopropyl)benzene melting at 76°-80°. Refluxing of this material with Darco in 425 ml of cyclohexane, followed by filtration, evaporation of the filtrate to 250 ml, seeding and then cooling to 8°-10°, gave 18.30 g of the product melting at 81.5-82°.

Anal. Calc'd for $C_{16}H_{20}N_2$: C, 79.95; H, 8.39; N, 11.66. Found: C, 78.98; 79.32 H, 8.46; 8.34 N, 11.69 11.54.

EXAMPLE 9

This example shows the preparation of a polyamide from 1,4-bis(2-methyl-2-cyanopropyl)benzene.

(a) Preparation of 1,4-Bis(2,2-dimethyl-3-aminopropyl)benzene

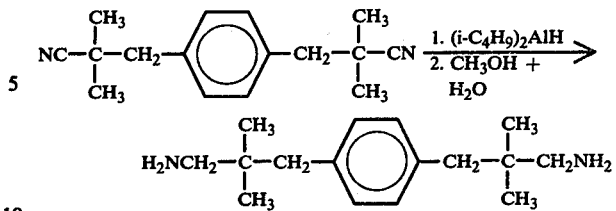

In a 2-liter flask, equipped with a magnetic stirrer, a reflux condenser capped with a nigrogen bubbler, and an additional funnel, was placed 7.50 g (0.0312 M) of 1,4-bis(2-methyl-2-cyanopropyl)benzene and 300 ml of reagent grade toluene which had been passed through acid alumina under nitrogen directly into the reaction vessel. With stirring at room temperature, 107 ml of a 24.1% solution (0.150 M) of diisobutylaluminum hydride in toluene was added from the addition funnel in 28 min. The mixture was then refluxed for 16 hrs. After the mixture had been cooled in an ice-water bath, a solution of 6 ml of water in 30 ml of methanol was added dropwise with stirring. This was followed by the dropwise addition of a solution of 30 ml of water in 60 ml of methanol. The mixture was stirred vigorously for 1 hr while being cooled in the ice-water bath, and then for an additional hour at room temperature. The mixture was filtered under nitrogen, the solid was washed thoroughly on the filter with toluene, and the combined filtrate and rinsings were distilled on the water pump. The resulting residue crystallized on cooling to room temperature. Further drying on the oil pump gave 5.28 g (68%) of crude 1,4-bis(2,2-dimethyl-3-aminopropyl)benzene melting at 53°-56° to a cloudy melt. Distillation of this material through a small Vigreux still gave the product as a colorless liquid boiling at 131°-132°/0.60 mm. The solidified material melted to a clear melt at 53.5–54.75°.

Anal. Calc'd for $C_{16}H_{28}N_2$: C, 77.36; H, 11.36; N, 11.28 C, 77.68; 77.07 77.15 H, 11.44; 11.30 11.27 N, 11.04 11.14.

The infrared spectrum contains bands at 2.93, 3.00 and 6.15μ (—NH₂), 3.28μ (shoulder) (≡CH), 3.38 and 3.48μ (saturated CH), 6.59 and 6.77μ (aromatic C=C), 7.21 and 7.33 μ (gemdimethyl), and 11.86μ (p-disubstituted aromatic).

(b) Preparation of a Polyamide from 1,4-Bis(2,2-dimethyl-3-aminopropyl)benzene and Sebacyl Chloride

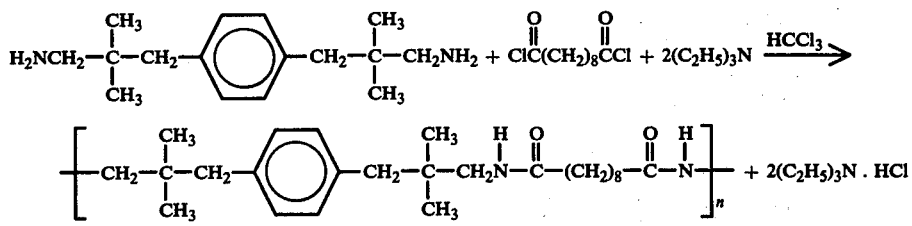

In a 3-liter flask, equipped with a paddle stirrer, a reflux condenser, and a nitrogen bubbler, was placed 25.00 g of 1,5-bis(2,2-dimethyl-3-aminopropyl)benzene, 31.0 ml of triethylamine, and 350 ml of chloroform which had been passed through basic alumina under nitrogen directly into the reaction flask. With vigorous stirring at room temperature, 24.07 g of freshly distilled sebacyl chloride in 100 ml of purified chloroform was added all at once. The mixture was stirred for 45 minutes and then 1500 ml of hexane was added to precipitate the polymer. After 15 minutes of stirring, the mixture was allowed to stand overnight. With stirring, a solution of 150 ml of concentrated hydrochloric acid in 600 ml of water was added. The coagulated polymer was filtered, rinsed on the filter with water, and then washed in a blender once with 600 ml of water, once with 600 ml of acetone and three times with 600 ml of 9(a). Upon distillation of the isolated product through a small Vigreux still, there was obtained 3.51 g of 1,3-bis(2,2-dimethyl-3-aminopropyl)benzene as a colorless liquid distilling at 105°–110°/0.05 mm.

Anal. Calc'd for $C_{16}H_{28}N_2$: C, 77.36; H, 11.36; N, 11.28. Found: C, 77.59; 77.29 H, 11.31; 11.23 N, 11.36; 11.50.

(b) Preparation of a Polyamide from 1,3-Bis(2,2-dimethyl-3-aminopropyl)benzene and Sebacyl Chloride

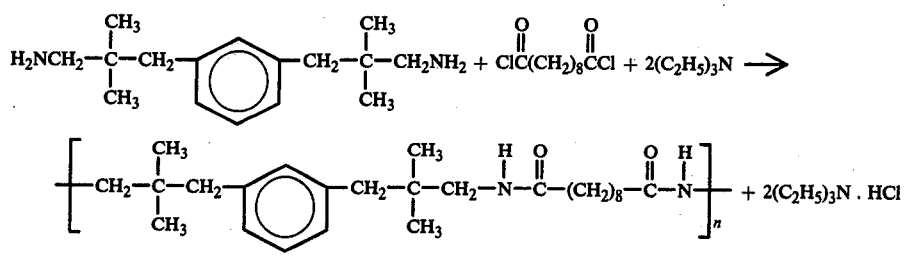

water. The isolated polymer was dried overnight in a vacuum oven at 70°. There was thus obtained 32.6 g (78%) of product: inherent viscosity (0.05% in m-cresol at 25°) = 1.32.

A clear, tough, colorless film was pressed at 180° and 500 lbs pressure from a portion of this polymer. Another portion of the polymer was melt spun through a spinnerette (0.020 inch × 0.04 inch) at 248° to 270° to give filament which, after cold drawing, had strengths of about 1.5 grams/denier.

The product of another experiment, on 1/10 the scale of that just described, was further characterized by elemental analysis and infrared spectroscopy.

Anal. Calc'd for $(C_{26}H_{42}N_2O_2)_n$: C, 75.31; H, 10.21; N, 6.76 Found: C, 75.20; 75.66 H, 10.90; 10.89 N, 6.94 6.95.

The infrared spectrum contained bands at 3.03μ(—NH), 3.42 and 3.48μ (saturated CH), 6.08 and 6.45μ (amide I and II bands), 6.60μ (aromatic C=C), and 7.30 and 7.32μ (gemdimethyl).

EXAMPLE 10

This example illustrates the preparation of a polyamide from 1,3-bis(2-methyl-2-cyanopropyl)benzene.

(a) Preparation of 1,3-Bis(2,2-dimethyl-3-aminopropyl)benzene

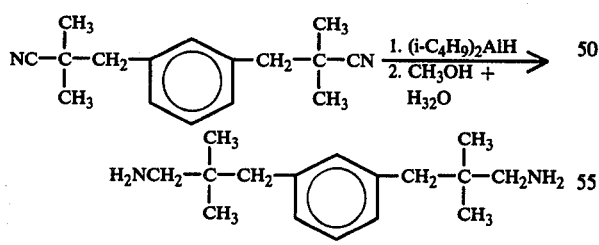

In a 1-liter flask, equipped with a paddle stirrer, a reflux condenser, capped with a nitrogen bubbler, and an addition funnel, was placed 7.50 g of 1,3-bis(2-methyl-2-cyanopropyl)benzene and 250 ml of reagent grade toluene which had been passed through acid alumina under nitrogen directly into the reaction vessel. With stirring at room temperature, 107 ml of a 25% solution of diisobutylaluminum hydride in toluene was added in 1 hr. The mixture was refluxed for 17 hrs 15 min. The mixture was then worked up as described in Example In a 300-ml flask, equipped with a paddle stirrer, a reflux condenser and a nitrogen bubbler, was put 4.00 g of 1,3-bis(2,2-dimethyl-3-aminopropyl)benzene, 5.00 ml of triethylamine, and 50 ml of chloroform which had been passed through basic alumina under nitrogen. With vigorous stirring, a solution of 3.85 g of sebacyl chloride (freshly distilled) in 25 ml of purified chloroform was added all at once. The mixture was stirred for 10 minutes and poured into 500 ml of hexane with stirring. Stirring was continued for a few minutes, the mixture was filtered, and the isolated solid was rinsed on the filter with hexane. The dried solid was washed in a blender once with 200 ml of water and once with 100 ml of acetone. The resulting sticky polymer was dried in a vacuum oven at room temperature and then washed in the blender three times with 200 ml of water. After being dried in a vacuum oven at 70°, the polymer weighed 3.20 g: inherent viscosity (0.05% in m-cresol at 25°) = 0.36.

EXAMPLE 11

This example illustrates the preparation of a polyamide from 1,4-bis(2-methyl-2-cyanopropyl)tetramethylbenzene.

(a) Preparation of 1,4-Bis(2,2-dimethyl-3-aminopropyl)tetramethylbenzene

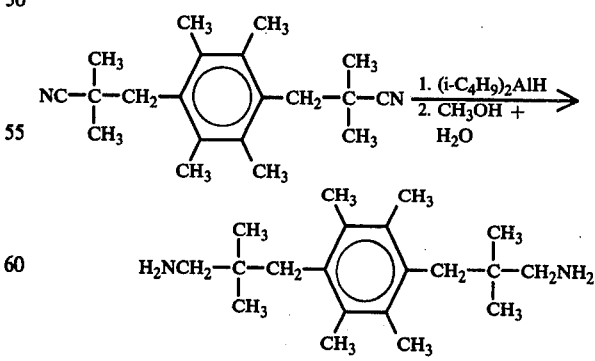

In a 1-liter flask, equipped as described in Example 9(a), was put 6.17 g of 1,4-bis(2-methyl-2-cyanopropyl)-tetramethylbenzene and 200 ml of reagent grade toluene which had been passed through acid alumina under nitrogen directly into the reaction vessel. With stirring at room temperature, 71.3 ml of a 24.1% solution of diisobutylaluminum hydride in toluene was added in 25 min. The mixture was refluxed for 22 hrs and allowed to stand at room temperature for 3 days. After the mixture had been cooled in an ice-water bath, a solution of 4 ml of water in 20 ml of methanol was added dropwise with stirring. This was followed by the dropwise addition of a solution of 20 ml of water in 40 ml of methanol. The mixture was then stirred at room temperature for several hours and allowed to stand at room temperature for 3 days. The mixture was filtered under nitrogen, the solid was washed thoroughly with toluene on the filter, and the combined filtrate and rinsings were distilled on the water pump. A solid residue resulted which, after further drying in a vacuum oven at room temperature, weighed 5.21 g and melted at 97°-99°. Sublimation of this material at 125°-145°/0.50 mm gave 1,4-bis(2,2-dimethyl-3-aminopropyl)tetramethylbenzene as a colorless crystalline solid melting at 97.5°-98.5°.

Anal. Calc'd for $C_{20}H_{36}N_2$: C, 78.88; H, 11.92; N, 9.20. Found: C, 78.62; 78.55 H, 12.05; 12.08 N, 9.89; 10.09.

The infrared spectrum contains bands at 2.96; 3.03, and 6.20$\mu$ (—$NH_2$), 3.38 and 3.43$\mu$ (saturated CH), 6.73$\mu$ (aromatic C=C), and 7.23 and 7.36$\mu$ (gem-dimethyl).

(b) Preparation of a Polyamide from 1,4-Bis(2,2-dimethyl-3-aminopropyl)tetramethylbenzene and Sebacyl Chloride In a 1-liter flask, equipped with a paddle stirrer, a reflux condenser, and a nitrogen bubbler, was placed 10.00 g of 1,4-bis(2,2-dimethyl-3-aminopropyl)tetramethylbenzene, 10.1 ml of triethylamine, and 125 ml of chloroform which had been passed through basic alumina under nitrogen. The reaction flask was cooled in a room-temperature water bath, and with vigorous stirring a solution of 7.85 g of freshly distilled sebacyl chloride in 50 ml of purified chloroform was added all at once. After the mixture had been stirred vigorously for another 30 minutes, 500 ml of hexane was added, and stirring was continued for 30 minutes. Then with stirring, 200 ml of water was added. Stirring was continued for a short time and the mixture was allowed to stand at room temperature overnight. The polymer was isolated by filtration, rinsed on the filter with water, and then washed in a blender once with 200 ml of water, once with 200 ml of acetone, and three times with 200 ml of water. The isolated polymer was dried overnight in a vacuum oven at 70°. There was thus obtained 9.50 g (61%) of product: inherent viscosity (0.05% in m-cresol at 25°) = 0.38. A clear, colorless, brittle film was pressed at 180° and 500 lbs pressure.

EXAMPLE 12

This example illustrates the preparation of a polyamide from 3,3'-bis(2-methyl-2-cyanopropyl)biphenyl.

(a) Preparation of 3,3'-Bis(2,2-dimethyl-3-aminopropyl)biphenyl

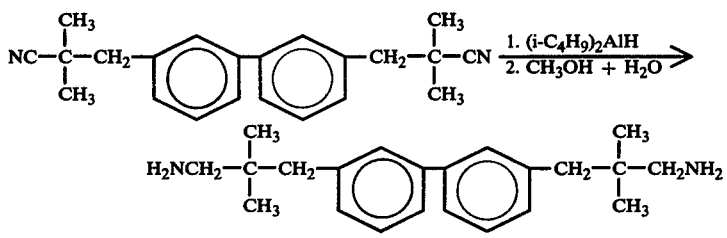

In a 2-liter flask, equipped as described in Example 9(a), was put 10.90 g of 3,3'-bis(2-methyl-2-cyanopropyl)biphenyl and 500 ml of reagent grade toluene which had been passed through acid alumina under nitrogen directly into the reaction vessel. With stirring at room temperature, 118 ml of a 25% solution of diisobutylaluminum hydride in toluene was added in 25 minutes. The mixture was refluxed for 18 hrs, and then allowed to stand at room temperature for 1 day. After the mixture had been cooled in an ice-water bath, a solution of 7 ml of water in 35 ml of methanol was added dropwise with stirring. This was followed by the dropwise addition of a solution of 33 ml of water in 66 ml of methanol. The ice-water bath was removed, and the mixture was stirred for 1 hour. The mixture was filtered under nitrogen, the solid was washed thoroughly with toluene on the filter, and the combined filtrate and rinsings were distilled on the water pump. The cloudy viscous residue weighed 10.8 g after it was evacuated for several hours with the oil pump at room temperature. Distillation of this material through a small Vigreux still gave 5.94 g of 3,3'-bis(2,2-dimethyl-

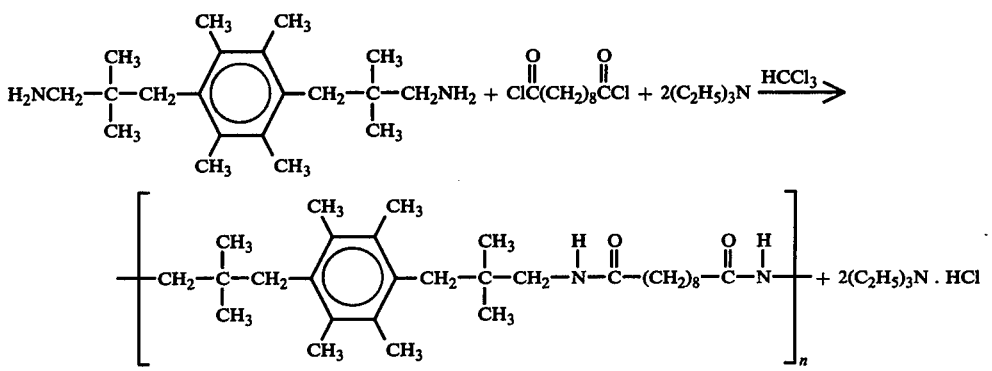

3-aminopropyl)biphenyl as a clear, colorless, viscous liquid boiling at 159°-168°/0.2-0.5 mm.

Anal. Calc'd for $C_{22}H_{32}N_2$: C, 81.42; H, 9.94; N, 8.63 Found: C, 81.31; 81.40 H, 10.19; 10.57 N, 8.29 8.47.

(b) Preparation of a Polyamide from 3,3'-Bis(2,2-dimethyl3-aminopropyl)biphenyl and Diphenyl Bibenzoate

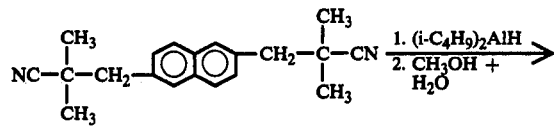

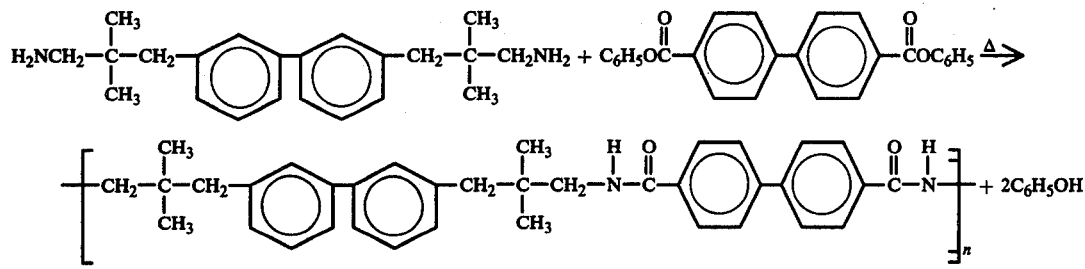

In a 50-ml round bottomed flask, flushed out with nitrogen, was placed 5.05 g of 3,3'-bis(2,2-dimethyl-3-aminopropyl)biphenyl and 6.14 g of diphenyl bibenzoate. The flask was then fitted with a 15 cm extension tube which had an adaptor for connecting to a nitrogen bubbler and for the insertion of a nitrogen capillary into the reaction vessel. The flask was then heated for 20 minutes in an oil bath at about 220° with the nitrogen capillary positioned above the reaction mixture. The capillary was then lowered so that nitrogen bubbled up through the reaction mixture and the heating at 220° continued for about 4 hours. The bath was then heated more strongly so that its temperature rose to 270° in the next hour. Heating at 270° was continued for 1 hr 30 min. During the final hour of the heating period, the flask was evacuated with an oil pump. The flask was then removed from the oil bath and allowed to cool to room temperature. The flask was broken and the polymer was isolated: weight = 8.2 (~ 100%) of clear, amber-colored, tough solid: inherent viscosity (0.05% in m-cresol at 25°) = 0.29.

Long tough fibers could be drawn from this polymer heated on a metal block at 300°-310°. A clear, colorless, tough film was pressed at 220° and 500 lbs pressure.

EXAMPLE 13

This example illustrates the preparation of a polyamide from 2,6-bis(2-methyl-2-cyanopropyl)naphthalene.

(a) Preparation of 2,6-Bis(2,2-dimethyl-3-aminopropyl)naphthalene

In a 1-liter flask, equipped as described in Example 10(a), was put 9.06 g of 2,6-bis(2-methyl-2-cyanopropyl)naphthalene and 300 ml of reagent grade toluene which had been passed through acid alumina under nitrogen directly into the reaction vessel. With stirring at room temperature, 107 ml of a 25% solution of diisobutylaluminum hydride in toluene was added in 55 minutes. The mixture was then refluxed for 20 hrs. After the mixture had been cooled in an ice-water bath, a solution of 6 ml of water in 30 ml of methanol was added with stirring during 55 minutes. This was followed by the addition of a solution of 30 ml of water in 60 ml of methanol during 1 hr 35 min. The mixture was stirred for 1 hr while being cooled in the ice-water bath and then at room temperature overnight. The mixture was filtered under nitrogen, the solid was washed thoroughly with toluene on the filter, and the combined filtrate and rinsings were distilled on the water pump. The resulting solid residue, after being dried in vacuo for about 2 hrs, weighed 8.0 g and melted at 97°-98.25°. Sublimation of this material at 145°-165°/0.6 mm gave 2,6-bis(2,2-dimethyl-3-aminopropyl)naphthalene as a colorless, crystalline solid melting at 96.75°-98.50°.

Anal. Calc'd for $C_{20}H_{30}N_2$: C, 80.48; H, 10.13; N, 9.39. Found: C, 82.09; 81.74 H, 10.45; 10.48 N, 9.85 9.77. The infrared spectrum contains bands at 2.98 and 3.06 μ (—NH$_2$), 3.29 μ (unsaturated CH), 3.38, 3.43 and 3.50 μ (saturated CH), 6.23, 6.65 and 6.80 μ (—NH$_2$ and/or aromatic C═C), and 7.22 and 7.33 μ (gem-dimethyl).

(b) Preparation of a Polyamide from 2,6-Bis(2,2-dimethyl-3-aminopropyl)naphthalene and Diphenyl Terephthalate

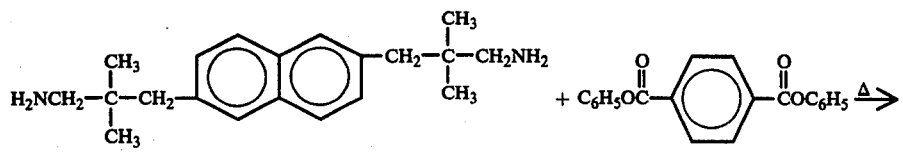

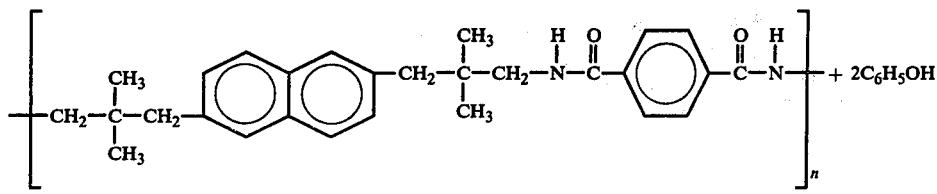

In a polymer tube (23 cm × 2.5 cm), fitted with a side arm and well flushed with nitrogen was put 5.00 g of 2,6-bis(2,2-dimethyl-3-aminopropyl)naphthalene and 5.33 g of diphenyl terephthalate. A nitrogen capillary was positioned in the tube so that the end of the capillary was above the reaction mixture. The tube was lowered into the vapor of a 220° vapor bath and heated at that temperature for 4 hrs 30 min. After 1 hr 15 min at 220°, the capillary was lowered so that the nitrogen bubbled up through the reaction mixture. The tube was then heated at 280° for 2 hrs 30 min. During the last 30 min of this heating, the tube was evacuated at about 2.5 mm. After the tube had cooled to room temperature, it was broken and the polymer was isolated: 5.61 g (78%), inherent viscosity (0.05% in mcresol at 25°) = 0.20.

EXAMPLE 14

This example illustrates the preparation of a polyamide from 4,4'-bis(2-methyl-2-cyanopropyl)biphenyl.

(a) Preparation of 4,4'-Bis(2,2-dimethyl-3-aminopropyl)-biphenyl

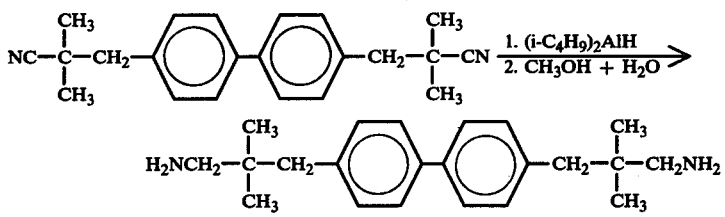

In a 1-liter flask, equipped as described in Example 10(a), was put 6.54 g of 4,4'-bis(2-methyl-2-cyanopropyl)biphenyl and 400 ml of reagent grade toluene which had been passed through acid alumina under nitrogen directly into the reaction vessel. With stirring at room temperature, 71 ml of a 25% solution of diisobutylaluminum hydride in toluene was added in 30 minutes. The mixture was then refluxed for 17 hrs 40 min. After the mixture had been cooled in an ice-water bath, a solution of 5 ml of water in 22 ml of methanol was added dropwise with stirring in 1 hr. This was followed by the dropwise addition of a solution of 20 ml of water in 40 ml of methanol in 1 hr. The mixture was stirred for 1 hr while being cooled in the ice bath and for 1 hr at room temperature. It then stood at room temperature for one day. The mixture was filtered under nitrogen, the solid was washed thoroughly with toluene on the filter, and the combined filtrate and rinsings were distilled on the water pump. The resulting solid, after drying in vacuo, weighed 5.5 g and melted at 97°–99°. Sublimation at 185°–200°/0.10 mm gave 4,4'-bis(2,2-dimethyl-3-aminopropyl)biphenyl as a colorless crystalline solid.

Anal. Calc'd for $C_{22}H_{32}N_2$: C, 81.42; H, 9.94; N, 8.63. Found: C, 81.31; 81.29 H, 10.11; 10.36 N, 8.87 8.68.

(b) Preparation of a Polyamide from 4,4'-Bis(2,2-dimethyl-3-aminopropyl)biphenyl and Diphenyl Bibenzoate

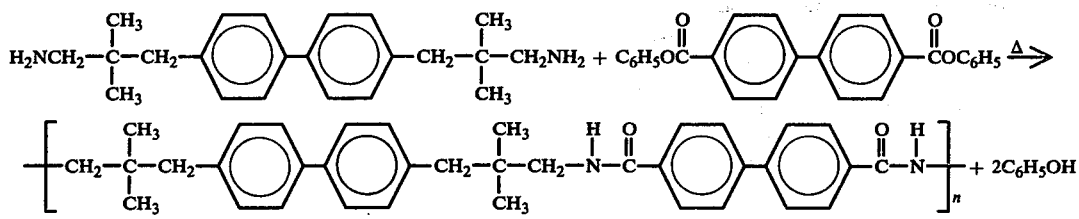

In a large test tube (30 cm × 3.5 cm), well flushed with nitrogen and fitted with a 2-hole rubber stopper containing a straight glass tube and a right angle glass tube, was put 4.0 g of 4,4'-bis(2,2-dimethyl-3-aminopropyl)-biphenyl and 4.86 g of diphenyl bibenzoate. A nitrogen capillary was fitted into the straight tube and positioned so that its end was above the reaction mixture. The right angle tube was connected to a nitrogen bubbler. The test tube was lowered into the vapor of a 220° vapor bath and heated at that temperature for 3 hrs 45 min. The tube was then heated in a 280° vapor bath for 1 hr 25 min. During the last 40 minutes the tube was evacuated with an oil pump. After the tube had cooled to room temperature, the polymer was isolated: 6.5 g (99%). Successive washings of the polymer in a blender with 100 ml of water, 100 ml of acetone, and then 3 times with 100 ml of water and then drying in a vacuum oven at 70° gave 6.16 g of product: inherent viscosity (0.05% in sulfuric acid at 25°) = 0.40.

We claim:

1. Aromatic-aliphatic dinitriles of the formula

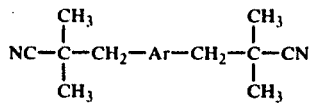

in which Ar is an arylene selected from the group consisting of 1,2-phenylenes, 1,3-phenylenes, 1,4-phenylenes, 2,2'-biphenylenes, 3,3'-biphenylenes, 4,4'-biphenylenes, 4,4'-phenyleneoxyphenylenes, 4,4'-phenylenemethylenephenylenes and 2,6-naphthylenes, said arylene being unsubstituted or substituted with halo, lower alkyl or phenyl.

2. The aromatic-aliphatic dinitrile of claim 1 in which Ar is 1,4-phenylene.

3. The aromatic-aliphatic dinitrile of claim 1 in which Ar is 1,3-phenylene.

4. The aromatic-aliphatic dinitrile of claim 1 in which Ar is 4,4'-biphenylene.

5. The aromatic aliphatic dinitrile of claim 1 in which Ar is 3,3'-biphenylene.

6. The aromatic-aliphatic dinitrile of claim 1 in which Ar is 2,6-naphthylene.

* * * * *